United States Patent [19]

Sobel

[11] Patent Number: 4,986,819
[45] Date of Patent: Jan. 22, 1991

[54] PRESSURE SENSITIVE NEEDLE GUARD

[76] Inventor: Daniel Sobel, 5 Hedge Ct., Snyder, N.Y. 14226

[21] Appl. No.: 412,739

[22] Filed: Sep. 26, 1989

[51] Int. Cl.⁵ .............................................. A61M 5/32
[52] U.S. Cl. ................................ 604/198; 604/263; 604/192
[58] Field of Search ............. 604/192, 197, 198, 263, 604/110

[56] References Cited

U.S. PATENT DOCUMENTS

| | | | |
|---|---|---|---|
| 3,658,061 | 4/1972 | Hall | 604/263 |
| 4,139,009 | 2/1979 | Alvarez | 604/198 |
| 4,725,267 | 2/1988 | Vaillancourt | 604/198 |
| 4,735,618 | 4/1988 | Hagen | 604/192 |
| 4,795,432 | 1/1989 | Karczmer | 604/198 |
| 4,804,371 | 2/1989 | Vaillancourt | 604/198 |
| 4,850,977 | 7/1989 | Bayless | 604/198 |
| 4,863,434 | 9/1989 | Bayless | 604/198 |
| 4,863,435 | 9/1989 | Sturman et al. | 604/198 |
| 4,892,521 | 1/1990 | Laico et al. | 604/198 |
| 4,894,055 | 1/1990 | Sudnak | 604/198 |
| 4,911,706 | 3/1990 | Levitt | 604/198 |
| 4,917,672 | 4/1990 | Teindrop et al. | 604/198 |

Primary Examiner—Stephen C. Pellegrino
Assistant Examiner—Michael Rafa

[57] ABSTRACT

The invention features a needle guard for a hypodermic syringe that will prevent repuncture by a used needle. The needle guard has a flexible membrane that expands when pressure actuated to cover and protect the injecting tip of the syringe needle. The membrane is characterized by a small, unobtrusive profile in the inactivated state.

18 Claims, 2 Drawing Sheets

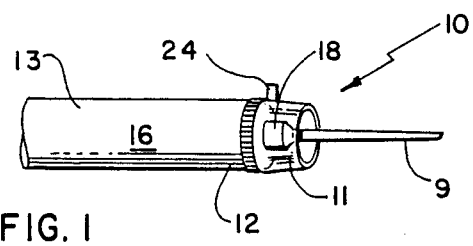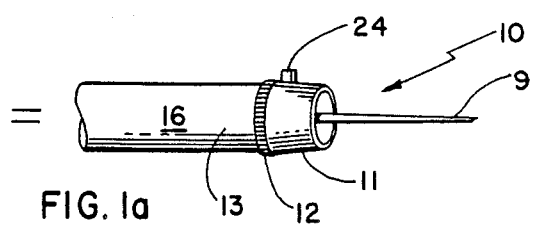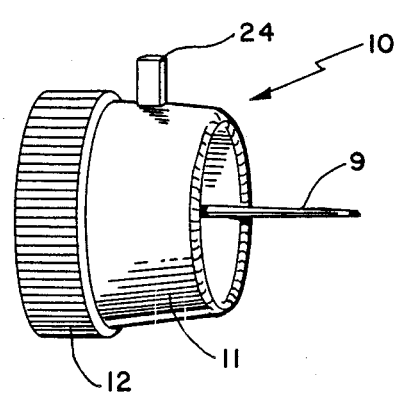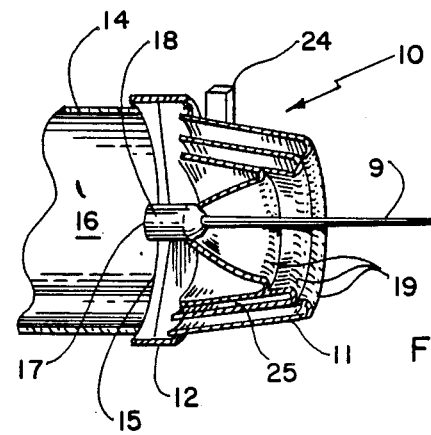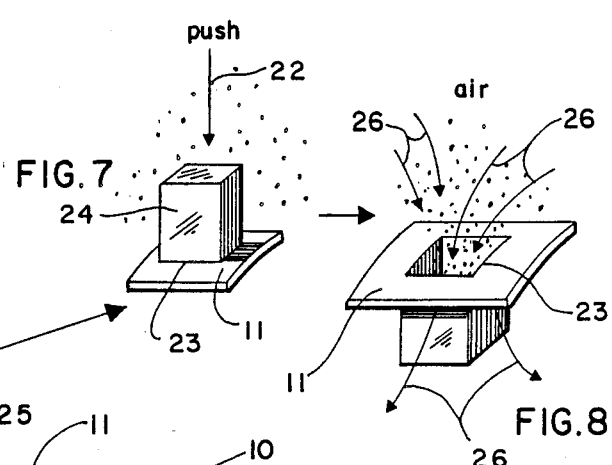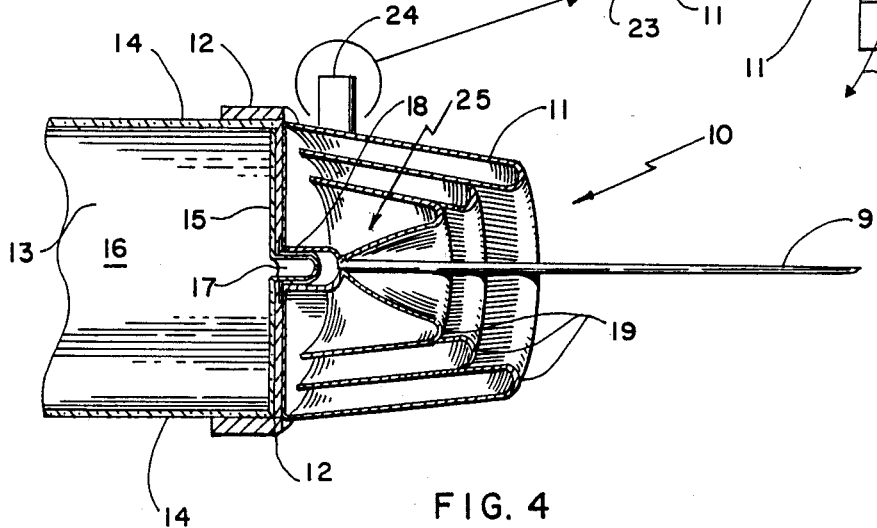

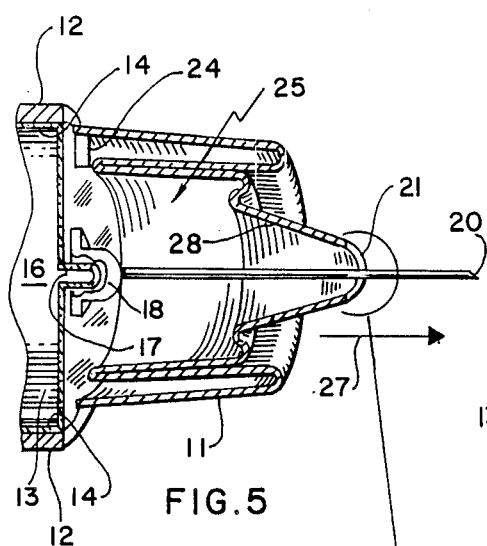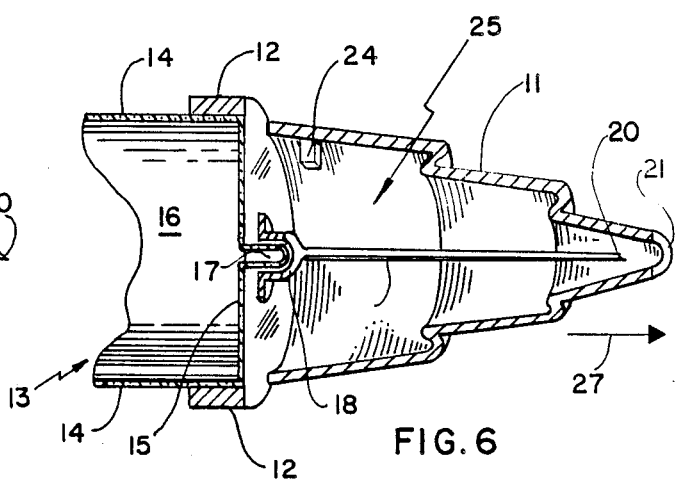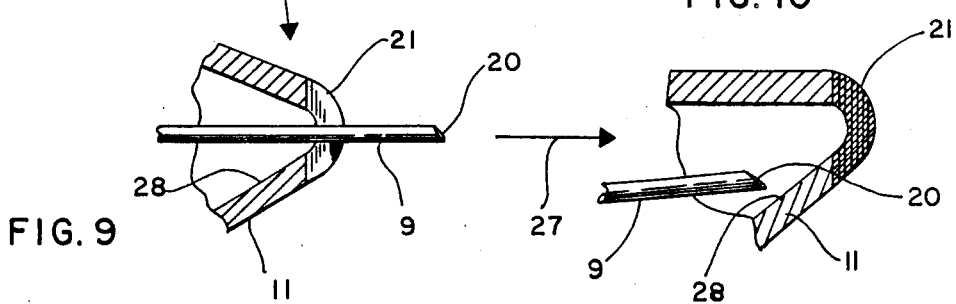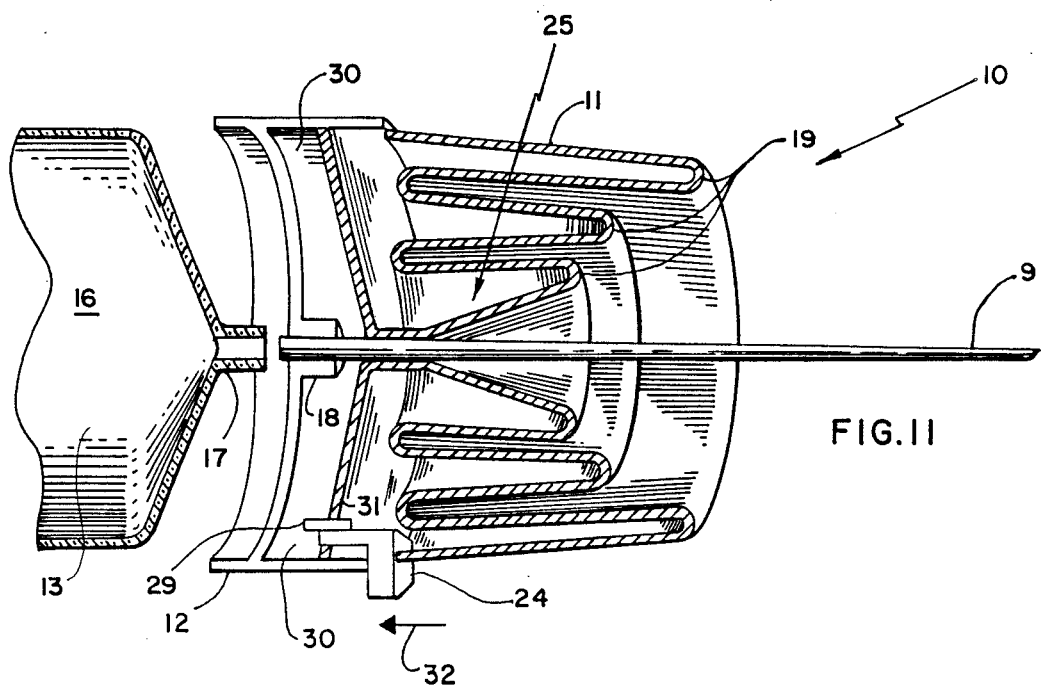

PRESSURE SENSITIVE NEEDLE GUARD

FIELD OF THE INVENTION

The invention relates to a protective covering for a hypodermic needle that prevents its reuse, and more particularly to a protective guard that is expandable to cover the injecting tip of a hypodermic needle in response to a change in pressure.

BACKGROUND OF THE INVENTION

In recent times, the need to prevent repuncture with a used syringe needle has become of paramount importance in view of the AIDS epidemic.

Laboratory personnel and doctors have become accidentally infected with the AIDS, HIV virus by puncturing themselves with needles used to inject or draw blood from an AIDS infected patient.

To prevent repuncture, many devices have been invented to cover the tip of the needle after use.

While all of these devices are useful and workable, many are bulky, unsightly and inconvenient to deploy.

Most of these prior art devices use a plastic sheath that is mechanically actuated either in a spring-like or hinge-like manner. These hinge-like units widen at their base to form a butterfly shape in their retracted position, which shape is both unsightly and bulky.

Such devices are shown in U.S. Pat. Nos. 4,139,009, issued: Feb. 13, 1979; and 4,735,618, issued: Apr. 5, 1988.

Some devices use a snap-over extension guard, such as that illustrated in U.S. Pat. No. 3,658,061, issued: Apr. 5, 1972. These type of devices are generally bulky and inconvenient to deploy.

The present invention seeks to provide a simple, reliable device for covering a hypodermic needle after its initial use, so that it cannot be reused.

The present invention also provides a new method of actuating the needle guard that allows the guard to assume a small profile in the retracted, inactivated state.

SUMMARY OF THE INVENTION

The invention features a pressure-sensitive needle guard for protecting against the reuse or repuncture of a hypodermic needle.

The needle guard comprises a small, folded membrane that fits upon the front end of a syringe and provides an unobtrusive appendage thereto. The membrane forms a sealed chamber that is either evacuated or that contains normal air pressure.

The needle guard also has means to repressurize or further pressurize the sealed chamber, causing the folded membrane to expand. As the membrane is caused to unfold into its expanded state, it achieves a position wherein it covers the puncture tip of the hypodermic needle.

The chamber is easily and conveniently pressurized by means of a simple push button that extends into the chamber to break a seal and introduce the pressure.

It is an object of the present invention to provide an improved needle guard for hypodermic syringes.

It is another object of the present invention to provide a needle guard having a small unobtrusive profile in the retracted, inactivated position.

It is a further object of this invention to provide a needle guard that can be made integral with the needle, so that both components can be mounted simultaneously.

BRIEF DESCRIPTION OF THE DRAWINGS

These and other objects of this invention will be better understood and will become more apparent with reference to the subsequent detailed description considered in conjunction with the accompanying drawings, in which:

FIG. 1 illustrates an in situ view of the needle guard of this invention, wherein the guard comprises transparent materials;

FIGURE 1a depicts the needle guard of FIG. 1 with opaque materials;

FIG. 2 is an enlarged view of FIG. 1a;

FIG. 3 is a cut-away, cross-sectional view of FIGURE 2;

FIG. 4 is a further enlarged view of FIG. 3, wherein the needle guard membrane is depicted in the inactivated, non-expanded state;

FIG. 5 is the needle guard of FIG. 4 shown in an initial state of actuation and expansion;

FIG. 6 illustrates the needle guard of FIG. 4 as it becomes fully expanded to cover the tip of the hypodermic needle;

FIG. 7 shows a perspective view of the push-button actuator shown in FIG. 4 in the inactivated position;

FIG. 8 depicts the push button of FIG. 7 in the actuated position corresponding to the initiation state illustrated in FIG. 5;

FIG. 9 is a blown-up view of the tip of the membrane and needle of FIG. 5;

FIG. 10 is a blown-up view of the tip of the membrane and needle corresponding to the expanded state of FIG. 6; and FIG. 11 is a cut-away, cross-sectional view of an alternate embodiment of the invention depicted in FIG. 4.

DETAILED DESCRIPTION OF THE PREFERRED EMBODIMENT

Generally speaking, the invention pertains to a needle guard for a hypodermic syringe that prevents the reuse or repuncture of the same needle after its initial use. The invention features a new method of pressure actuation, which is quick, reliable and convenient, and which allows the design of the guard to have a small, unobtrusive profile.

For the sake of brevity like components shall have the same designation throughout the figures.

Now referring to FIG. 1, the needle guard 10 of this invention is shown in situ. The needle guard 10 comprises a transparent, flexible plastic membrane 11 having a rigid collar 12 that fits over the peripheral portion 14 of the front end 15 of the barrel 13 of a hypodermic syringe 16. (See FIG. 4.) The hypodermic needle 9 passes through the center of the plastic membrane 11 and attaches to the nose abutment 17 of syringe 16 via a slide-on cap 18.

The membrane 11 may be attached to the syringe 16 via collar 12 after or before the placement of the needle cap 18 on the nose abutment 17 of the syringe 16, or the membrane 11 can be fabricated as an integral unit with the needle 9 and attached simultaneously therewith.

The membrane 11 can also be formed from an opaque plastic material as shown in FIG. 1a. The transparent membrane 11 of FIG. 1, however, is preferred, since it provides a view of the needle 9 after the membrane has expanded (FIG. 6). This provides the advantage of informing the personnel responsible for disposing of this medical waste product that a dangerous needle 9 is disposed therein.

FIGS. 2 and 3 illustrate, in enlarged views, the respective needle guards 10 shown in FIG. 1a and 1.

The membrane 11 shown in FIGS. 1, 1a, 2, 3 and 4 is in the retracted, inactivated state. This membrane 11 placed upon the front end 15 of barrel 13 of syringe 16 provides a small unobtrusive mechanism, the operation of which will be explained hereinafter with reference to FIGS. 4 through 10.

Referring to FIG. 3, an enlarged view of membrane 11 is shown. Membrane 11 comprises a number of folds 19. A further enlarged view of the folds 19 of membrane 11 can be seen with reference to FIG. 4.

Membrane 11 is fabricated from a flexible plastic, which allows it to expand when the needle guard 10 is actuated, but which is tough enough to prevent the tip 20 of the needle 9 from penetrating therethrough, as illustrated in FIG. 10. A plastic useful for this purpose can be a polyethylene or a polypropylene.

The folded membrane 11 defines a vacuated chamber 25. The vacuum in chamber 25 keeps the membrane 11 in its folded retracted position, as shown in FIG. 4.

After injection by needle 9, the holder of the syringe 16 will actuate the needle guard 10, by pressing a pushbutton 24 inwardly (arrow 22), as depicted in enlarged detail in FIG. 7. This inward push will rupture a small window seal 23 on the surface of membrane 11, causing air to rush into (arrows 26) the vacuated chamber 25 (FIG. 8).

Referring to FIG. 5, the membrane 11 is shown expanding outwardly (arrow 27) under the influence of the air pressure now being exerted on the folded inner walls 28 of chamber 25.

Under the influence of increasing air pressure, the membrane 11 will continue to expand until fully expanded, as illustrated in FIG. 6.

In its fully expanded position (FIG. 5), membrane 11 will form a cone-shaped structure.

The end 21 of membrane 11 defines a hole, which the tip 20 of needle 9 passes through, as the membrane expands (arrow 27) and achieves its full expanded length, as shown in FIGS. 6, 9 and 10.

The expanded membrane 11 expands asymmetrically, such that the hole 21 through which the needle 9 originally passes will not be available for repassage of the needle 9 backwardly therethrough.

In this way the tip 20 of needle 9 comes to rest against the inner wall 28 of membrane 11, wherein it is shielded from repuncturing personnel that handle the used syringe 16.

Now referring to FIG. 11, an alternate embodiment of the needle guard 10 of FIGS. 1-10 is illustrated.

The needle guard 10' of FIG. 11 features an additional chamber 30 that is built into the rigid plastic collar 12.

This chamber 30 is filled with compressed gas, such as air or $CO_2$, which gives a pressure boost to expansion of membrane 11 by filling the vacuated chamber 25.

This expansion boost is accomplished by rupturing a seal 29 in rigid wall 31 defining the compressed gas chamber 30. The compressed gas chamber 30 will then flow into evacuated chamber 25, thus providing a higher pressure force causing a more rapid expansion of membrane 11.

The rupture of seal 29 is accomplished by pushing (arrow 32) upon L-shaped button 24', which will be caused to break seal 29, as shown.

Having thus described the invention, what is desired to be protected by Letters Patent is presented in the subsequent appended claims.

Since other modifications and changes varied to fit particular operating requirements and environments will be apparent to those skilled in the art, the invention is not considered limited to the example chosen for purposes of disclosure, and covers all changes and modifications which do not constitute departures from the true spirit and scope of this invention.

What is claimed is:

1. A pressure-sensitive needle guard for preventing needle-stick or reuse of a hypodermic needle attached to a forward portion of a barrel of a hypodermic syringe, comprising:
   an expandable guard member that is positionable upon the forward portion of said barrel of said hypodermic syringe, said expandable guard member being movable between a first, non-expanded position wherein said hypodermic needle is free to cause a puncture, and a second, expanded position wherein said guard has expanded to cover said tip of said hypodermic needle, said expandable guard member including an internal pressure-sensitive chamber means which when pressurized causes said guard member to expand to said second, expanded condition.

2. The pressure-sensitive needle guard of claim 1, wherein said hypodermic needle is integrally attached to said guard member.

3. The pressure-sensitive needle guard of claim 1, further comprising a flexible expandable membrane defining said pressure-sensitive chamber means.

4. The pressure-sensitive needle guard of claim 3, wherein said flexible expandable membrane is folded upon itself in said first, non-expanded position.

5. The pressure-sensitive needle guard of claim 4, wherein said flexible expandable membrane includes a plurality of folds which under pressure expand to a cone-shaped member.

6. The pressure-sensitive needle guard of claim 1, wherein said internal pressure-sensitive chamber means defines a vacuum-sealed membrane in said first non-expanded position, and a membrane having a ruptured seal in said second, expanded position.

7. The pressure-sensitive needle guard of claim 1, further comprising a pressurized means contiguously disposed adjacent said internal, pressure-sensitive chamber means, for pressurizing said internal, pressure-sensitive chamber means and causing said guard member to expand to said second, expanded condition.

8. The pressure-sensitive needle guard of claim 6, further comprising a pressurized means contiguously disposed adjacent said internal, pressure-sensitive chamber means, for pressurizing said internal, pressure-sensitive chamber means and causing said guard member to expand to said second, expanded condition.

9. A pressure-sensitive needle guard for protecting against the reuse or repuncture of a hypodermic needle, comprising:
   chamber means defining a pressure-sensitive chamber that is flexibly expandable when pressurized, and is expandable in a pressurized condition to cover a puncture tip of said hypodermic needle; and means for pressurizing said chamber means for causing said chamber means to expand and cover said puncture tip of said hypodermic needle.

10. The pressure-sensitive needle guard of claim 9, wherein said chamber means further comprises a flexibly, expandable membrane.

11. The pressure-sensitive needle guard of claim 10, wherein said membrane is folded upon itself in a non-expanded condition.

12. The pressure-sensitive needle guard of claim 10, wherein said membrane forms a cone-shaped member in an expanded condition.

13. The pressure-sensitive needle guard of claim 9, wherein said chamber means includes an expandable membrane comprising a vacuum seal.

14. The pressure-sensitive needle guard of claim 13, wherein the means for pressurizing said chamber means comprises rupture means for rupturing said vacuum seal.

15. The pressure-sensitive needle guard of claim 9, wherein said needle guard is integral with said hypodermic needle.

16. The pressure-sensitive needle guard of claim 15, further comprising a base member adjacent said chamber means for attachment to a syringe.

17. The pressure-sensitive needle guard of claim 9, wherein said means for pressurizing said chamber means includes a push-button.

18. A pressure sensitive needle guard comprising a folded, flexibly expandable membrane defining an interior pressure chamber said membrane characterized in that the membrane expands to a puncture protective position in response to a change of internal pressure in said chamber.

* * * * *